United States Patent [19]

Russ et al.

[11] Patent Number: 4,537,766
[45] Date of Patent: Aug. 27, 1985

[54] LONG-WEARING EYESHADOW COMPOSITIONS

[75] Inventors: Julio G. Russ, Germantown; Donna L. Barrom, Arlington, both of Tenn.

[73] Assignee: Plough, Inc., Memphis, Tenn.

[21] Appl. No.: 589,033

[22] Filed: Mar. 12, 1984

Related U.S. Application Data

[63] Continuation of Ser. No. 463,196, Feb. 2, 1983, abandoned, which is a continuation-in-part of Ser. No. 286,108, Jul. 22, 1981, abandoned.

[51] Int. Cl.$^3$ ............................................. A61K 7/021
[52] U.S. Cl. ................................ 424/63; 424/DIG. 5; 514/772; 514/785
[58] Field of Search ...................... 424/DIG. 5, 63, 64, 424/358

[56] References Cited

U.S. PATENT DOCUMENTS

| | | | |
|---|---|---|---|
| 3,088,876 | 5/1963 | Buth | 424/64 |
| 3,211,105 | 10/1975 | Papantoniou et al. | 424/64 |
| 3,211,618 | 10/1965 | Kambersky | 514/787 |
| 4,336,246 | 6/1982 | Leon-Pekarek | 424/70 |
| 4,383,875 | 5/1983 | Russ et al. | 424/64 X |
| 4,431,673 | 2/1984 | Goldner et al. | 424/63 X |

FOREIGN PATENT DOCUMENTS 2014852  9/1979  United Kingdom ..... 424/DIG. 5 X

OTHER PUBLICATIONS

Balsam et al., Cosmetics: Science and Technology, 2nd Ed., Wiley, vol. 1, pp. 398–407.
Syncrowaxes–Structural Synthetic Waxes Derived from Vegetable Oil, G. J. Brooks, Croda, Inc., 2/12/80.
Crodats, Subject: Syncrowax, 1/25/79, Published by Croda Inc.
Croda Formulas, C747, C748, and C791.

*Primary Examiner*—Sidney Marantz
*Assistant Examiner*—Shawn P. Foley
*Attorney, Agent, or Firm*—Gerald S. Rosen; Warrick E. Lee, Jr.; Stephen I. Miller

[57] ABSTRACT

An eyeshadow composition comprising candelilla wax, $C_{18-36}$ acid triglyceride, third wax having melting point between 55° and 100° C., volatile nonaqueous solvent, cosmetically acceptable oil, and pigment.

18 Claims, No Drawings

LONG-WEARING EYESHADOW COMPOSITIONS

This is a continuation of Ser. No. 463,196 filed Feb. 2, 1983, now abandoned, which in turn is a continuation-in-part of Ser. No. 286,108, filed July 22, 1981, now abandoned.

The present invention relates to eyeshadow compositions that may be formed into sticks for easy, non-messy application. More specifically, the present invention relates to eyeshadow compositions that are resistant to creasing, that is, gaps in surface coating, after being coated on the eyelids. The compositions may be molded into sticks for use in familiar swivel or push-up dispensers or encased in wooden or plastic cylinders to form pencils. When in pencil form, the compositions form points easily for precise application. Both the sticks and pencil points have good structural strength and breakage resistance.

Prior art eyeshadow sticks tend to show creasing during normal wear after a short time. Attempts to alleviate this problem by adding and/or subtracting ingredients have resulted in compositions that are too dry, hard, tacky, or greasy. Other prior compositions are unmoldable or crystallize into separate phases, rendering the composition unsightly and unusable. For example, a composition prepared in accordance with Croda Formula MU-36-1 Eyeshadow Stick, published by Croda, Inc., showed excessive crystallization upon stability testing. This crystallization rendered the composition unsightly.

Surprisingly, we have discovered a composition containing previously-known cosmetic ingredients in specific concentrations that produces a highly-acceptable, long-wearing eyeshadow. The compositions have good stability and a consistency that is acceptable for use on the eyelids.

Buth, U.S. Pat. No. 3,088,876 discloses lipstick formulations containing ingredients that are similar to those of the present invention. Buth's examples 4 and 5 are believed pertinent to our invention. However, formulations prepared in accordance with those examples were too sticky to be comfortable after application to the eyelids.

The present invention provides an eyeshadow stick composition that is moldable and has good structural strength, long shelf life and consistency suitable for use as an eyeshadow. Preferred formulations are crease-proof, i.e. they will not crease for 8 hours after application.

In its broadest aspect, the present invention comprises an eyeshadow composition comprising:
(a) 2 to 30 percent candelilla wax,
(b) 2 to 30 percent $C_{18-36}$ acid triglyceride having a melting point between about 70° and and 75° C. wherein the acid groups contain an average of about 28 carbon atoms,
(c) 2 to 30 percent wax other than (a) or (b) having melting point between 55° and 100° C.,
wherein the total amount of (a), (b), and (c) is 10 to 50 percent,
(d) 5 to 50 percent volatile, non-aqueous solvent for (a), (b), and (c),
(e) 5 to 50 percent cosmetically acceptable oil, and
(f) 5 to 50 percent of at least one pigment.

The most preferable choice for ingredient (c) is microcrystalline wax having melting point of about 75° C.

The compositions are preferably anhydrous.

Unless otherwise specified, definitions of ingredients used in the compositions may be found in the CTFA Cosmetic Ingredient Dictionary, Second Edition, Published by the Cosmetic, Toiletry and Fragrance Association, Inc., 1133 Fifteenth Street, N.W., Washington, D.C. 20005. The relevant contents of this dictionary are incorporated herein by reference.

Unless stated otherwise, all percents are weight percents based on the total weight of the composition.

The preferred form of the composition is a cosmetic "stick" which is intended to include cosmetic sticks and pencils. However, alternate forms of the compositions, other than stick form are contemplated. For example, the composition may be poured or filtered into compacts or tubes and applied to the eyelids with the fingertips or an application device such as a sponge or cotton tipped wand.

DETAILED DESCRIPTION OF THE INVENTION

The compositions of the present invention comprise three selected waxes in acceptable concentrations.

THE FIRST WAX is candelilla wax. The first wax is present in the composition in the amount of 2 to 30 percent, more preferably 5 to 25 percent, and most preferably 7 to 20 percent.

THE SECOND WAX is $C_{18-36}$ acid triglyceride, that is, a tri-ester of glycerine and $C_{18-36}$ fatty acids. The average number of carbon atoms in the acid groups is about 28. The second wax has a melting point between about 70° and 75° C. An acceptable second wax is sold under the tradename SYNCROWAX HGL-C by Croda, inc., 51 Madison Ave., New York, N.Y. A description of $C_{18-36}$ acid triglyceride, including a typical theoretical structure, appears in *Syncrowaxes-Structural Synthetic Waxes Derived from Vegetable Oil* by G. J. Brooks, published by Croda, Inc., which is incorporated herein by reference to the extent pertinent. The second wax is present in the composition in the amount of 2 to 30 percent, more preferably 5 to 25 percent and most preferably 7 to 20 percent.

The term used for the second wax, that is, "$C_{18-36}$ acid triglyceride" has been adopted by the Cosmetic, Toiletry, and Fragrance Association, Inc. for the third Edition of the CTFA Cosmetic Ingredients Dictionary.

THE THIRD WAX is a wax other than the first or second waxes having melting point between 55° and 100° C. (more preferably 60°-85° C. and most preferably 70° to 80° C.). The third wax renders the structural strength of the composition higher than it would be without the third wax. Suitable third waxes, may be of animal origin, such as bees wax; vegetable origin, such as carnauba; or mineral origin, such as ozokerite, paraffin, microcrystalline wax or Japan wax. The third wax could also be synthetic, such as polyethylene wax or polyethylene wax copolymer. Combinations of waxes are also acceptable as the third wax.

The amount of the third wax in the composition is 2 to 30 percent, more preferably 4 to 25 percent, and most preferably 4 to 20 percent.

Suitable third waxes include microcrystalline wax sold by International Wax Refining Co. Inc., Valley Stream, N.Y.; Eskar waxes (tradename) sold by America Oil, Co., Chicago, Ill.; wax, white, ozokerite, sold by Strahl and Pitsch, West Babylon, N.Y.; and A-C Copolymers (tradename) sold by Allied Chemical Company, Morristown, N.J. Of the above, microcrystalline wax is most preferred.

The total amount of the three waxes in the composition must be 10 to 50 percent, with 15 l to 35 percent being more preferable and 18 to 30 percent being most preferable.

The compositions contain 5 to 50 percent volatile, nonaqueous solvent for the 3 waxes. The solvent softens the waxes allowing easy application of the compositions onto the body in a thin layer. After application, the solvent evaporates leaving a highly-desirable, coating. More preferably the amount of solvent is 15 to 50 percent, and most preferably 20 to 40 percent. Preferably the solvent has a 100 percent evaporation time, in seconds, by ASTM test method D3539 of 4000 to 13,000 (more preferably 5000 to 12,000 most preferably 5,500 to 10,000).

Suitable solvents include SDA alcohols, volatile silicons, isoparaffinic hydrocarbons such as Isopar H, Isopar K, and Isopar L, sold by Esson, Houston, Tex.; Soltrol 130, sold by Phillips Petroleum Co., Bartlesville, OK; and petroleum distillates such as Shell Sol 71, sold by Shell Chemical Co., Houston, Tex. Other acceptable solvents are Ashland Odorless and Low Odor Mineral Spirits, sold by Ashland Chemical Co., Columbus, Ohio; and Penn-Drake No. 2251 Oil, sold by Penreco, Butlar, PA.

The cosmetic sticks will contain 5 to 50 percent cosmetically acceptable oil, more preferably 7 to 25 percent, and most preferably 10 to 20 percent. The preferred oils are mineral oil, lanolin alcohol, and mixtures thereof. Other oils such as mink oil, lanolin oil, propylene glycol, silicones, etc. are acceptable.

Pigments for coloring the eye-lids are included in the compositions. Typical pigments and colorants may include at least one of iron oxide, titanium dioxide, titanium coated mica, mica, talc, bismuth oxychloride, pigmented pearls, FD&C and D&C colors, mango violet, ultra marine colors, chrome oxide colors, carmine, ferric ammonium ferrocyanide, and so on. The amount of pigment and colorant may be 5 to 80 percent, more preferably 5 to 50 percent, still more preferably 10 to 40 percent, and most preferably 10 to 35 percent. The pigments should be acceptable for use near the eye.

Other ingredients may improve certain properties of the compositions. Approximately 0.5 percent preservatives and antioxidants such as methyl, butyl, or propyl paraben, BHA and BHT prevent degradation by microorganisms or oxidation.

For greater shelf life it is preferred that the compositions be packaged in airtight or nearly airtight containers such as pencils with tight fitting caps or swivel or push-up containers with tight covers. This prevents premature evaporation of the solvent.

Additionally, at least a portion of the solvent may be microencapsulated or entrapped in a polymer matrix. When the composition is rubbed on the body, the capsules or matrix ruptures, releasing the solvent. It may also be desirable to encapsulate or entrap the oil, pigments, and/or pearls. Hence, as used throughout the present specification and claims, amounts of solvent, oil, pigments, and pearls in the composition is intended to include, not only free ingredients, but also those which are encapsulated and/or entrapped.

EXAMPLE I

An eyeshadow having the following composition is prepared:

| INGREDIENT | WEIGHT % |
|---|---|
| First wax: Candelilla wax | 7.0 |
| Second wax: $C_{18-36}$ acid triglyceride[1] | 7.0 |
| Third wax: Microcrystalline wax | 5.0 |
| Petroleum distillate | 40.0 |
| Oil[2] | 10.2 |
| Preservatives and antioxidants | 0.5 |
| Pigments | 30.3 |
| TOTAL | 100 |

1. Syncrowax HGL-C (Tradename)
2. Mixture of mineral oil and lanolin alcohol sold under the tradename of Protolan M-16 by Protameen Chemicals, Inc., Totawa, N.J.

The three waxes are melted in a kettle. The oil, preservatives and antioxidants are added to the kettle and thoroughly mixed in. The pigments are pulverized, screened and added to the mixture with good mixing. The batch is cooled to about 70° C. and the petroleum distillate is mixed in with the kettle covered. The mixture is heated to about 85° C. and molded in chilled molds.

EXAMPLE II

An eyeshadow having the following composition is prepared:

| INGREDIENT | WEIGHT % |
|---|---|
| First wax: Candelilla wax | 9.0 |
| Second wax: $C_{18-36}$ triglyceride[1] | 15.0 |
| Third wax: Microcrystalline wax | 4.0 |
| Petroleum distillate | 25.0 |
| Oil[1] | 18.2 |
| Preservative and antioxidants | 0.5 |
| Pigments | 28.3 |
| TOTAL | 100 |

1. Same ingredient as in Example I.

The ingredients are blended and molded by the procedure of Example I.

EXAMPLE III

An eyeshadow having the following composition is prepared:

| INGREDIENT | WEIGHT % |
|---|---|
| First wax: candelilla wax | 8.5 |
| Second wax: $C_{18-36}$ acid triglyceride[1] | 9.5 |
| Third wax: microcrystalline wax | 7.5 |
| Petroleum distillate | 34.0 |
| Oil[1] | 14.8 |
| Preservative and antioxidants | 0.5 |
| Pigments | 25.2 |
| TOTAL | 100 |

1. Same ingredient as in Example I.

The ingredients are blended and molded by the procedure of Example I.

The compositions of Examples I, II, and III mold well into sticks or leads. When applied to the eyelids, they form desirable, long-wearing coatings.

COMPARATIVE EXAMPLE

Example III is repeated except that Stabelite Ester No. 5 is used in place of $C_{18-36}$ acid triglyceride. Stabelite Ester No. 5 is a triester of glycerine and rosin, believed to contain an average of $C_{20}$, having a softening point of about 81° C. Stabelite Ester No. 5, one of the ingredients used by Buth in U.S. Pat. No. 3,088,876, differs from the $C_{18-36}$ acid triglyceride required by the invention in that acid groups do not contain enough carbons (average of 20 versus about 28 required by this invention) and its melting point is too high (about 81° C. versus about 70° to 75° C.). The composition made with Stabelite Ester No. 5 would not mold. It was too sticky and lacking in structure to form a stick or pencil. This example illustrates the criticality of applicant's choice of waxes.

What is claimed is:

1. An eyeshadow composition comprising by weight:
   (a) 2 to 30 percent candelilla wax,
   (b) 2 to 30 percent $C_{18-36}$ acid triglyceride having a melting point between about 70° and 75° C. wherein the acid groups contain an average of about 28 carbon atoms,
   (c) 2 to 30 percent wax other than (a) or (b) having a melting point between 55° and 100° C.;
   wherein the total amount of (a), (b), and (c) is 10 to 50 percent by weight of the eyeshadow composition,
   (d) 5 to 50 percent volatile, non-aqueous solvent for (a), (b), and (c),
   (e) 5 to 50 percent cosmetically acceptable oil, and
   (f) 5 to 50 percent of at least one pigment.

2. The composition of claim 1 containing:
   5 to 25 percent (a),
   5 to 25 percent (b),
   4 to 25 percent (c),
   wherein the total amount of (a), (b), and (c) is 15 to 35 percent by weight of the eyeshadow composition,
   15 to 50 percent (d), and
   7 to 25 percent (e).

3. The composition of claim 2 containing:
   7 to 20 percent (a),
   7 to 20 percent (b),
   4 to 20 percent (c),
   wherein the total amount of (a), (b), and (c) is 18 to 30 percent by weight of the eyeshadow composition,
   20 to 40 percent (d), and
   10 to 20 percent (e).

4. The composition of claim 3 wherein (c) is microcrystalline wax.

5. The composition of claim 3 wherein (e) is mineral oil, lanolin alcohol, or a mixture thereof.

6. The composition of claim 3 wherein (d) has a 100 percent evaporation time of 4,000 to 13,000 seconds as measured by ASTM test method D 3539.

7. The composition of claim 6 wherein the 100 percent evaporation time of (d) is 5,000 to 12,000 seconds.

8. The composition of claim 7 wherein the 100 percent evaporation time of (d) is 5,500 to 10,000 seconds.

9. The composition of claim 1 wherein (c) has a melting point of 60° to 85° C.

10. The composition of claim 9 wherein (c) has a melting point of 70° to 80° C.

11. An eyeshadow stick or pencil made from the composition of claim 1 consisting of:
    (a) 9 percent candelilla wax,
    (b) 15 percent $C_{18-36}$ acid triglyceride having a melting point between about 70° and 75° C. wherein the acid groups contain an average of about 28 carbon atoms,
    (c) 4 percent microcrystalline wax,
    (d) 25 percent petroleum distillate,
    (e) 18.2 percent oil consisting of mineral oil, lanolin alcohol or a mixture thereof,
    (f) 28.3 percent pigment, and
    (g) 0.5 percent preservative and antioxidant.

12. The eyeshadow stick or pencil of claim 11 wherein the 100 percent evaporation time of (d) is 5,500 to 10,000 as measured by ASTM test method D 3539.

13. An eyeshadow stick or pencil packaged in an airtight container, said eyeshadow comprising by weight:
    (a) 7 to 20 percent candelilla wax,
    (b) 7 to 20 percent $C_{18-36}$ acid triglyceride having a melting point between about 70° and 75° C. wherein the acid groups contain an average of about 28 carbon atoms,
    (c) 4 to 20 percent microcrystalline wax,
    wherein the total amount of (a), (b), and (c) is 18 to 30 percent by weight of the eyeshadow composition,
    (d) 20 to 40 percent petroleum distillate having a 100 percent evaporation time of 5,500 to 10,000 seconds as measured by ASTM test method D 3539,
    (e) 10 to 20 percent of mineral oil, lanolin alcohol, or a mixture thereof, and
    (f) 10 to 35 percent of at least one pigment.

14. An eyeshadow stick or pencil according to claim 13 consisting of:
    (a) 7 percent candelilla wax,
    (b) 7 percent $C_{18-36}$ acid triglyceride having a melting point between about 70° and 75° C. wherein the acid groups contain an average of about 28 carbon atoms,
    (c) 5 percent microcrystalline wax,
    (d) 40 percent petroleum distillate,
    (e) 10.2 percent oil consisting of mineral oil, lanolin alcohol or a mixture thereof,
    (f) 30.3 percent pigment, and
    (g) 0.5 percent preservative and antioxidant.

15. The eyeshadow stick or pencil of claim 14 wherein the 100 percent evaporation time of (d) is 5,500 to 10,000 seconds as measured by ASTM test method D 3539.

16. The eyeshadow stick or pencil of claim 14 wherein the 100 percent evaporation time of (d) is 5,500 to 10,000 seconds as measured by ASTM test method D 3539.

17. An eyeshadow stick or pencil according to claim 13 consisting of:
    (a) 8.5 percent candelilla wax,
    (b) 9.5 percent $C_{18-36}$ acid triglyceride having a melting point between about 70° and 75° C. wherein the acid groups contain an average of about 28 carbon atoms,
    (c) 7.5 percent microcrystalline wax,
    (d) 34 percent petroleum distillate,
    (e) 14.8 percent oil consisting of mineral oil, lanolin alcohol or a mixture thereof,
    (f) 25.2 percent pigment, and
    (g) 0.5 percent preservatives and antioxidant.

18. A method of formulating a crease-resistant eyeshadow composition of claim 1, comprising the step of combining the ingredients therein in a non-aqueous solvent.

* * * * *